United States Patent
Koslow et al.

Patent Number: 6,077,588
Date of Patent: *Jun. 20, 2000

[54] CONTINUOUS SOLID STATE WEB COATING PROCESS AND WEBS PRODUCED THEREBY

[75] Inventors: Evan E. Koslow, Weston; Richard D. Kendrick, Stratford; Gordon Spilkin, Stamford, all of Conn.

[73] Assignee: Koslow Technologies Corporation, Orange, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/903,395

[22] Filed: Jul. 22, 1997

Related U.S. Application Data

[62] Division of application No. 08/813,055, Mar. 7, 1997, Pat. No. 5,792,513.

[51] Int. Cl.[7] .............................. B32B 5/12; A61F 13/15
[52] U.S. Cl. ........................... 428/114; 428/74; 428/137; 604/359; 604/366; 604/367; 604/370; 604/372; 604/373; 604/378; 442/59
[58] Field of Search ............................. 428/74, 114, 137; 442/315.9, 59; 604/359, 366, 367, 370, 372, 373, 375, 378

[56] References Cited

U.S. PATENT DOCUMENTS

| | | | |
|---|---|---|---|
| T886,010 | 5/1971 | Craven et al. | 442/374 |
| 4,055,184 | 10/1977 | Karami | 604/359 |
| 4,420,590 | 12/1983 | Gartner | 525/357 |
| 4,547,195 | 10/1985 | Jackson | 604/359 |
| 4,626,252 | 12/1986 | Nishizawa et al. | 604/372 |
| 4,692,161 | 9/1987 | Puletti et al. | 604/366 |
| 4,872,870 | 10/1989 | Jackson | 604/366 |
| 5,055,332 | 10/1991 | Rhodes et al. | 428/74 |
| 5,147,722 | 9/1992 | Koslow | 428/402 |
| 5,151,301 | 9/1992 | Kruger et al. | 427/294 |
| 5,328,450 | 7/1994 | Smith et al. | 604/366 |
| 5,342,333 | 8/1994 | Tanzer et al. | 604/359 |
| 5,360,419 | 11/1994 | Chen et al. | 604/374 |
| 5,413,747 | 5/1995 | Akers et al. | 264/211 |
| 5,462,538 | 10/1995 | Korpman | 604/366 |
| 5,672,419 | 9/1997 | Mukaida et al. | 604/366 |
| 5,681,305 | 10/1997 | Korpman | 604/359 |

OTHER PUBLICATIONS

Microthene ®F Microfine Polyolefin Powders, U.S.I. Chemicals booklet, copyright 1980.

*Primary Examiner*—Cathy F. Lam
*Attorney, Agent, or Firm*—Ohlandt, Greeley, Ruggiero & Perle

[57] ABSTRACT

One or more particulate active agents are fused to the surface of a substrate web by mixing the particulate agents with a particulate binder having a particle size not exceeding an average diameter of approximately 40 microns and coating the composite mixture onto the surface of the substrate. Thereafter, the coated substrate is heated to a temperature equal to or greater than the Vicat softening temperature of the binder and compressed within the nip of a pair of pressure rolls to achieve fusion. If desired, a top layer may be placed upon the coated composite prior to the compression step. Also disclosed are various products manufactured by the process.

15 Claims, 1 Drawing Sheet

CONTINUOUS SOLID STATE WEB COATING PROCESS AND WEBS PRODUCED THEREBY

This application is a division of application Ser. No. 08/813,055, filed Mar. 7, 1997, now U.S. Pat. No. 5,792,513.

TECHNICAL FIELD

This invention relates to a novel method for the continuous production of a web coated with a layer of a powdered active substance. The active substance is caused to adhere to the web by means of a thermoplastic binder present in a sufficiently small volume that it does not interfere with the adsorbent or otherwise desirable characteristics of the active material.

BACKGROUND ART

The closest known processes to that of this invention are described in Koslow U.S. Pat. Nos. 5,019,311; 5,147,722; 5,189,092; 5,249,948; and 5,331,037, their parent applications, their corresponding foreign patent applications and patents, and the references cited therein.

The above-mentioned patents disclose processes for the production of composite materials which are characterized by primary particles interconnected by a binder material. Some of these processes require high pressure and shear or extrusion through a die with carefully controlled back pressure. These prior art processes are extremely useful in producing a wide variety of articles including extruded solid forms such as activated carbon filters.

It would often be desirable to impregnate, cover, or otherwise treat a relatively fragile web base material with an active component such as a powdered adsorbent or absorbent material. One example would be a nonwoven medium coated with agents having water absorption and odor adsorption characteristics as in a diaper or hygiene product. A number of other related products will be apparent to those skilled in the art such as, for example, coated paper tissues and toweling, and fabrics such as surgical bandages and sanitary napkins. However, the fragile nature of the underlying base material would make it impractical to employ the known prior art techniques which require high pressure and shear.

In the prior art referred to above, the powdered active material is formed into a self-supporting structure by fusion of a thermoplastic material with which it is intimately mixed. However, the pressures, temperatures, and shear involved, or the process equipment used would not permit their application to fragile substrates such as the webs described herein. Accordingly, it is a primary object of the present invention to provide a method for continuously coating a relatively fragile web with a dry mixture of at least one particulate active material and a very finely divided particulate thermoplastic binder. Other objects, features, and advantages will become apparent from the following description and appended claims.

DISCLOSURE OF INVENTION

In accordance with the present invention a loose, dry composite powder is formed which comprises at least one group of particles of an active ingredient and particles of a thermoplastic binder. The binder particles are quite small in size, preferably on the order of 20 microns and no greater than approximately 40 microns on average. The particle size of the active ingredient may be much larger, within the range, for example, of 5–5000 microns. The small size of the thermoplastic binder particles causes them to adhere to the particles of the active ingredient by electrostatic and van der Waal forces. In addition to their tendency to stick to the active particles, the binder particles also have a high innate cohesion.

The mixture of active and binder powders is applied to the surface of a moving web by means of a knurled roller. The coated web, which can be preheated through a convective or infra-red oven, is then passed through the nip of a pair of rollers, one of which is heated, which apply both heat and pressure to fuse the thermoplastic binder to the active particles and to the underlying web. This step may also be employed to incorporate a second web to achieve a sandwich effect with the active material incorporated between two web surfaces. Upon leaving the heated rollers, the thermoplastic binder sets to form a single, composite structure.

BEST MODE FOR CARRYING OUT THE INVENTION

Figure 2:
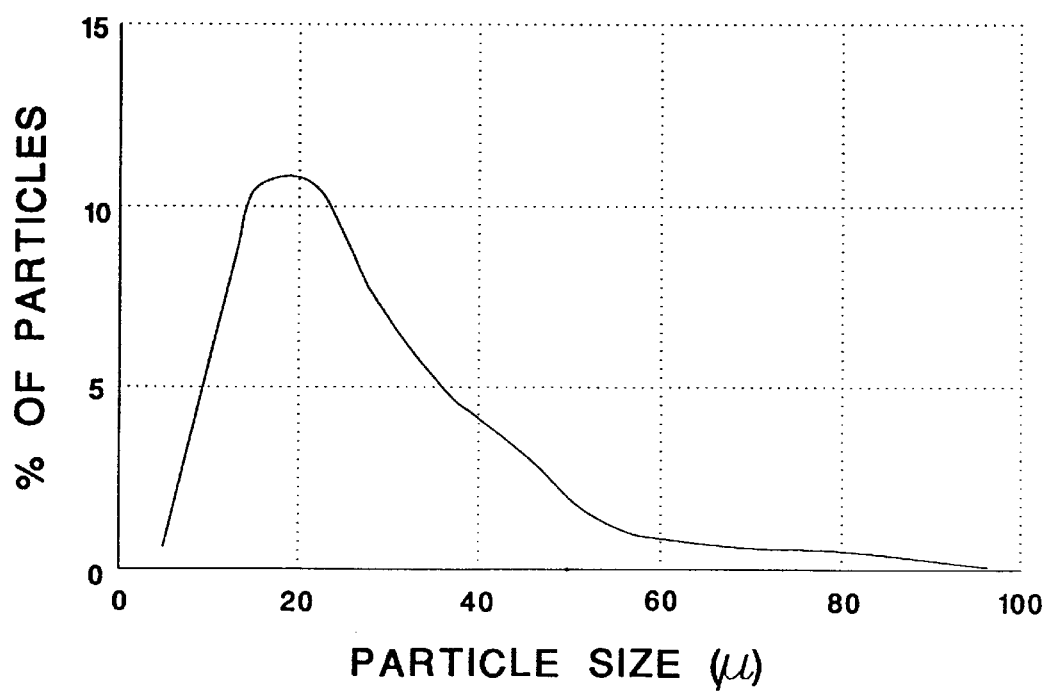
FIG. 2 is a graph showing the typical particle size distribution of a binder usable in this invention.

As has been described above, any of a large number of active particulate agents may be applied to an underlying web in accordance with this invention. Essentially the only limitation relates to the activity desired, e.g. liquid absorption, odor adsorption, medicament delivery, etc. The critical features of this invention, however, reside in the thermoplastic binder which is employed to coalesce the active particles and adhere them to the underlying web. For this purpose, the thermoplastic binder must be in the form of very small particles and must be present in a small enough volume that they do not interfere with the functioning of the active agent. Preferably, the binder will have an effective diameter of not more than 40 microns on average with an optimum size of 20 microns on average. A binder which is suitable for the process of this invention may be produced from normally solid, synthetic organic polymeric thermoplastic resins by the method disclosed in U.S. Pat. No. 3,432,483 of Peoples, et al. Examples of suitable binders are Microthene® F, microfine polyolefin powders produced by Quantum Chemical Company, such as, for example, their low density polyethylene designated FN-510 and their ethylene-vinyl acetate copolymer designated FE-532. FIG. 2 illustrates the typical particle size distribution of Microthene FN-510 powder.

Figure 1:
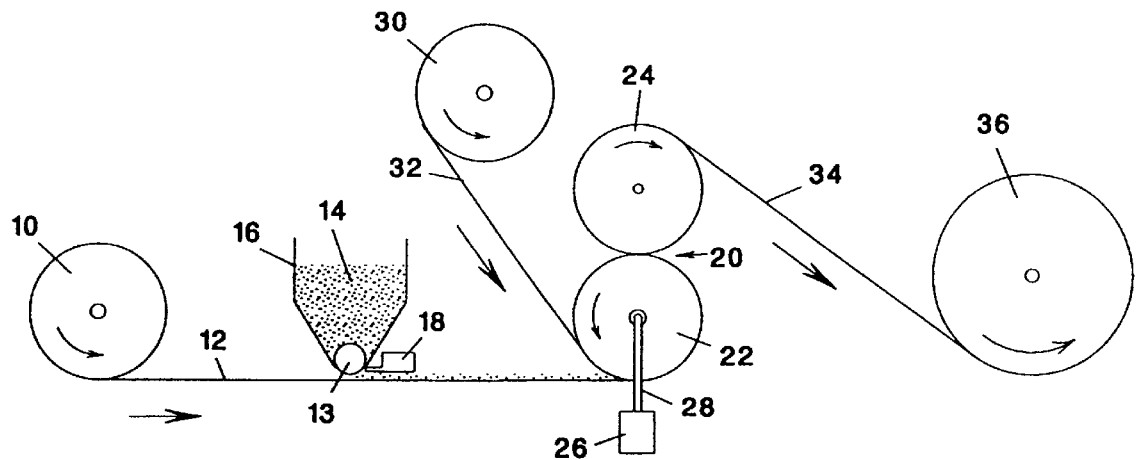
FIG. 1 is a schematic diagram illustrating an apparatus for the practice of the method of this invention.

FIG. 1 illustrates an exemplary apparatus for the practice of this invention. A supply roll 10 provides a web 12 of the substrate to be treated, such as a nonwoven tissue or towelling paper. Downstream from supply roll 10 is a knurled roller 13 positioned to receive the composite powder 14 of this invention from a hopper 16 and apply the powder to the upper surface of the web 12. The surface of the knurled roller 13 may be designed to provide a substantially continuous coating or, alternatively, a coating of a specific design such as, for example, stripes on the web surface. A brush 18 may be employed to aid in removing the composite powder from the knurled roller 13. Thereafter, the web 12 is passed through the nip 20 between a heated idler roller 22 and a drive roller 24. A pneumatic cylinder 26 is connected via a rod 28 to the axle of the idler roller 22 to maintain a desired pressure on the web within the nip 20. In passing over the surface of the heated roller 22, the binder is heated to a temperature equal to or greater than its Vicat softening temperature as it enters the nip 20. Within this nip the binder material fuses under pressure with the active material and with the material of the web. In the illustrated apparatus there is provided a second supply roll 30 of a web 32 which may be of the same or a different material from that of base web 12. This web is also passed between the nip 20 of the rollers 22, 24 and on the top of the particulate material which is being fused. Accordingly, the web 34 which leaves the roller 24 is a composite with both a top and bottom sheet, film, or nonwoven layer. Upon leaving the nip 20, the binder cools and hardens, thereby forming the desired composite. The composite web 34 passes onto a takeup roll 36. Some specific examples of the process of this invention are as follows.

Note: The Vicat softening temperature is defined by Quantum Chemical Company, Cincinnati, Ohio, as ". . . the temperature at which the finished [thermoplastic] article becomes too soft to withstand stresses and keep its shape. It is the temperature at which a flat-ended needle of 1 mm cross section under a load of 1 kg penetrates 1 mm into a . . . specimen. In the Vicat test, the temperature of the specimen is increased at a uniform rate."

EXAMPLE 1
Iodine Paper.

Iodine paper has utility when used, for example, in a filter unit as a germicidal element.

Both the substrate and the upper layer were 23 cm wide webs of 0.8 oz./sq. yd.spun bonded polyester identified as REEMAY type 2016. The production apparatus is as generally shown in FIG. 1 and described above.

The powder mixture consisted of 10% by weight ethylene-vinyl acetate copolymer, (FE532 of Quantum Chemical Company, Cincinnati, Ohio) and 90% by weight iodinated ion exchange resin, 47.5% iodine, balance inert, approximately 20–50 mesh particle size (Grade A605 PURADINE™ iodinated resin from The Purolite Company, Bala Cynwyd, Pa.).

The webs moved at the rate of 0.6 m/min and the composite powder was laid down in the amount of 0.02–0.07 g/cm$^2$. The heated roller was 10 inches in diameter and heated by hot oil to a temperature of 135° C. The binder reached its Vicat softening temperature of 75–80° C. in the nip. Pressure in the nip was maintained at approximately 70 kg/cm The product was a composite medium of good strength and porosity containing nearly 85% by weight of iodated resin The fact that the resin is not dry prior to processing did not have a significant impact on the quality of the product.

EXAMPLE 2
Carbon/Soda Paper.

Carbon and sodium-bicarbonate impregnated paper has particular utility as an odor removing component in, for example, an odor adsorbing sheet used in air filtration applications.

The apparatus was substantially identical to that of Example 1. However, the composite powder comprised 17% FE-532. The remaining 83% was 50% 80–325 mesh (500-44$\mu$) activated carbon and 50% 30–40$\mu$ particles of sodium bicarbonate (NaHCO$_3$). The web was run at a speed of 0.6–0.9 m/min and powder was deposited at the rate of 0.015 g/cm$^2$. The heated roller was at a temperature of 138° C. Three impregnated papers having the same widths as in Example 1 were successfully obtained with (i) both the upper and lower substrates consisting of cellulosic tissue, (ii) both the upper and lower substrates consisting of cellulosic towel stock, and (iii) the lower substrate consisting of cellulosic towel stock and the upper substrate layer consisting of cellulosic tissue stock.

EXAMPLE 3
Carbon Air or Liquid Filter Paper.

This adsorbent medium has utility in any situation where carbon treatment of either air or liquid is desirable.

The apparatus was similar to that of Example 1. The lower and upper substrates were both spun bonded polypropylene, (TYPAR grade 135 of Reemay Corporation). The powder mixture was 30% by weight FE-532 and 70% coconut carbon of 80-325 mesh (500-44$\mu$). The heated drum was at a temperature of 150° C. and the web speed was 0.6–1.0 m/min. The composite powder was deposited in the amount of 0.015 g/cm$^2$. This adsorbent medium was suitable for air filtration. The process was repeated substituting a bituminous coal based carbon for the coconut carbon. The resulting composite medium was optimal for water filtration applications. Both materials were entirely stable when operated in water and did not release fines.

EXAMPLE 4
Manganese Oxide Paper.

This paper has utility as a filter for removal of heavy metals, such as lead.

The apparatus was substantially identical to that of the preceding examples. Both the lower substrate and the upper layer comprised 25 cm wide CASTLE® facing spun bonded polypropylene from Kimberly-Clark Corporation. The powder mixture was 17% FE-532 and 83% MnO$_2$ of average particle size approximately 44$\mu$. Web speed was 0.8–1.5 m/min. Powder lay-down was 0.015 g/cm$^2$ and the heated drum temperature was 135° C. The resulting composite medium retains the manganese dioxide in its fully active state where it is capable of oxidizing and precipitating lead, cadmium and other heavy metals.

EXAMPLE 5
Super-Absorbent Composite.

This product has utility in absorbing liquids and might be used, for example, in diapers.

The apparatus was similar to those described in the preceding examples. Both the lower substrate and the upper layer comprised spun bonded polypropylene from Kimberly-Clark Corporation. The powder mixture was 10% FE-532 and 90% FavorSorb® 880 (a super absorbent acrylic-based polymer obtained from Stockhausen Corporation, Greensboro, NC. Two runs were made as follows, with production of suitable, super-absorbent composites:

(a) The composite powder laydown was 0.015 g/cm$^2$. Web speed was 0.8 m/min, the temperature of the heated drum was 138° C., and pressure was approximately 100 psi.

(b) The composite powder laydown was 0.36 g/cm$^2$. Web speed was 0.5–0.6 m/min, the temperature of the heated drum was 177° C., and pressure was approximately 100 psi.

This produced a composite medium having excellent water absorption characteristics.

It is believed that the many advantages of this invention will now be apparent to those skilled in the art. It will also be apparent that a number of variations and modifications may be made therein without departing from its spirit and scope. Accordingly, the foregoing description is to be construed as illustrative only, rather than limiting. This invention is limited only by the scope of the following claims.

What is claimed is:

1. A first substrate web having a first surface upon which is deposited a particulate iodinated resin and particles of a thermoplastic binder fused to both of said particulate resin and said first surface.

2. The web of claim 1 comprising, in addition, a second substrate web having a second surface spaced from said first substrate web and fused to said thermoplastic binder.

3. A first substrate web having a first surface upon which is deposited particulate sodium bicarbonate and particles of a thermoplastic binder fused to both of said particulate sodium bicarbonate and said first surface.

4. The web of claim 3 comprising, in addition, a second substrate web having a second surface spaced from said first surface and fused to said thermoplastic binder.

5. A first substrate web having a first surface upon which is deposited particulate manganese oxide and particles of a thermoplastic binder fused to both of said particulate manganese oxide and said first surface.

6. The web of claim 5 comprising, in addition, a second substrate web having a second surface spaced from said first surface and fused to said thermoplastic binder.

7. A composite structure comprising a first substrate having a first surface upon which is deposited a composite powder, said composite powder having particulate carbon and particles of a thermoplastic binder, wherein said particles of a thermoplastic binder coalesces said particulate carbon, and wherein said particles of a thermoplastic binder adhere said particulate carbon to said first surface.

8. The composite structure of claim 7 comprising, in addition, a second substrate having a second surface spaced from said first surface and fused to said thermoplastic binder.

9. A composite structure comprising a first substrate having a first surface upon which is deposited a composite powder, said composite powder having particles of a polymer liquid absorbent and particles of a thermoplastic binder, wherein said particles of a thermoplastic binder coalesces said particles of a polymer liquid absorbent, and wherein said particles of a thermoplastic binder adhere said particles of a polymer liquid absorbent to said first surface.

10. The composite structure of claim 9 comprising, in addition, a second substrate having a second surface spaced from said first surface and fused to said thermoplastic binder.

11. A composite web comprising:
a substrate web having a surface;
a composite powder mixture deposited on the surface of the substrate web in an amount up to about 0.36 g/cm$^2$, the composite powder mixture comprising:
about 5 to 30 weight percent thermoplastic binder particles which have an effective diameter in the range of about 5 to 95 microns, and
about 70 to 95 weight percent active agent particles having an effective diameter in the range of about 5 to 5000 microns,
wherein the thermoplastic binder particles are fused to the surface of the substrate web and the active agent particles.

12. The composite web of claim 11, wherein the thermoplastic forming the thermoplastic binder particles is a polyolefin.

13. The composite web of claim 11, wherein the substrate web is formed from a material selected from the group consisting of polyesters, polypropylene, cellulosic tissue stock and cellulosic towel stock.

14. The composite web of claim 11, wherein the active agent particles are selected from the group consisting of particulate activated carbon, particulate iodinated resin, particulate sodium bicarbonate, particulate manganese dioxide and particulate polymer liquid absorbents.

15. The composite web of claim 11, wherein the thermoplastic forming the thermoplastic binder particles is a polyolefin, wherein the substrate web is formed from a material selected from the group consisting of polyesters, polypropylene, cellulosic tissue stock and cellulosic towel stock, and wherein the active agent particles are selected from the group consisting of particulate activated carbon, particulate iodinated resin, particulate sodium bicarbonate, particulate magnese oxide and particulate polymer liquid absorbents.

* * * * *

(12) EX PARTE REEXAMINATION CERTIFICATE (7332nd)
United States Patent
Koslow et al.

(10) Number: US 6,077,588 C1
(45) Certificate Issued: Jan. 26, 2010

(54) CONTINUOUS SOLID STATE WEB COATING PROCESS AND WEBS PRODUCED THEREBY

(75) Inventors: Evan E. Koslow, Weston, CT (US); Richard D. Kendrick, Stratford, CT (US); Gordon Spilkin, Stamford, CT (US)

(73) Assignee: KX Technologies LLC, Orange, CT (US)

Reexamination Request:
No. 90/009,280, Sep. 18, 2008

Reexamination Certificate for:
Patent No.: 6,077,588
Issued: Jun. 20, 2000
Appl. No.: 08/903,395
Filed: Jul. 22, 1997

Related U.S. Application Data

(62) Division of application No. 08/813,055, filed on Mar. 7, 1997, now Pat. No. 5,792,513.

(51) Int. Cl.
*A61F 13/15* (2006.01)
*B01J 20/28* (2006.01)
*B05D 1/00* (2006.01)
*B05D 3/12* (2006.01)
*B05D 1/28* (2006.01)
*B05D 5/06* (2006.01)
*B05D 1/30* (2006.01)
*B32B 27/12* (2006.01)
*B32B 37/14* (2006.01)
*B32B 37/24* (2006.01)
*D06N 3/04* (2006.01)
*D21H 25/00* (2006.01)
*D21H 19/58* (2006.01)
*D21H 23/00* (2006.01)
*D21H 23/64* (2006.01)
*D21H 21/14* (2006.01)
*D21H 19/00* (2006.01)
*D21H 25/06* (2006.01)
*D06N 3/00* (2006.01)

(52) U.S. Cl. ............. 428/114; 428/137; 428/74; 442/59; 604/366; 604/370; 604/373; 604/378; 604/372; 604/367; 604/359

(58) Field of Classification Search .............. None
See application file for complete search history.

(56) References Cited

U.S. PATENT DOCUMENTS 5,328,450 A 7/1994 Smith et al.
6,077,588 A 6/2000 Koslow et al.

FOREIGN PATENT DOCUMENTS

EP 0 721 024 7/1996
WO WO 94/06296 3/1994

*Primary Examiner*—Krisanne Jastrzab

(57) ABSTRACT

One or more particulate active agents are fused to the surface of a substrate web by mixing the particulate agents with a particulate binder having a particle size not exceeding an average diameter of approximately 40 microns and coating the composite mixture onto the surface of the substrate. Thereafter, the coated substrate is heated to a temperature equal to or greater than the Vicat softening temperature of the binder and compressed within the nip of a pair of pressure rolls to achieve fusion. If desired, a top layer may be placed upon the coated composite prior to the compression step. Also disclosed are various products manufactured by the process.

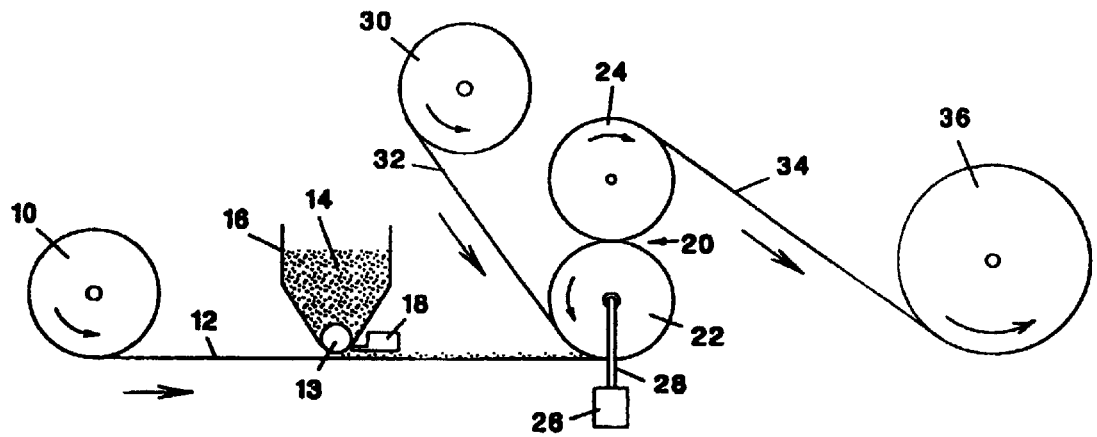

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 2 are cancelled.

New claims 16 and 17 are added and determined to be patentable.

Claims 3–15 were not reexamined.

*16. A first substrate web having a first surface upon which is deposited a composite powder mixture of particulate iodinated resin intermixed with particles of a thermoplastic binder, whereby said thermoplastic binder of said composite powder mixture is fused to both of said particulate resin and said first surface.*

*17. The web of claim 16 comprising, in addition, a second substrate web having a second surface spaced from said first substrate web and fused to said thermoplastic binder.*

* * * * *